United States Patent

Klotz et al.

[11] 4,132,896
[45] Jan. 2, 1979

[54] METHOD OF FORMING LAYERED IMAGES OF OBJECTS FROM SUPERPOSITION IMAGES OF DIFFERENT IMAGE PLANES

[75] Inventors: Erhard Klotz, Halstenbek; Ulf Tiemens, Prisdorf, both of Fed. Rep. of Germany

[73] Assignee: U.S. Philips Corporation, New York, N.Y.

[21] Appl. No.: 785,969

[22] Filed: Apr. 8, 1977

[30] Foreign Application Priority Data

Apr. 15, 1976 [DE] Fed. Rep. of Germany ....... 2616714

[51] Int. Cl.² .................... A61B 6/02; G03B 41/16
[52] U.S. Cl. .................... 250/445 T; 250/407
[58] Field of Search .................... 250/313, 314, 445 T, 250/407

[56] References Cited

U.S. PATENT DOCUMENTS

| | | | |
|---|---|---|---|
| 2,207,867 | 7/1940 | Loebell | 250/313 |
| 3,746,872 | 7/1973 | Ashe | 250/313 |
| 4,023,037 | 5/1977 | Weiss et al. | 62/196 |

FOREIGN PATENT DOCUMENTS

| | | | |
|---|---|---|---|
| 2546785 | 4/1977 | Fed. Rep. of Germany | 250/313 |
| 2547868 | 4/1977 | Fed. Rep. of Germany | 250/313 |
| 2306463 | 10/1976 | France | 250/313 |

*Primary Examiner*—Alfred E. Smith
*Assistant Examiner*—T. N. Grigsby
*Attorney, Agent, or Firm*—Thomas A. Briody; Jack E. Haken

[57] ABSTRACT

A method for forming a layered image of a three-dimensional object which is irradiated from different directions by a plurality of radiation sources. n coded superposition images, in different image planes, of a single movement phase are sequentially recorded on a mechanically moved detector face. Decoding of the n superposition images is realized by means of a coordinate matrix whose coordinates correspond to the geometry of the radiation source distribution, so that these images are successively electronically superposed and summed, for a number of times which equals the number of radiation sources. The same layer of the object is decoded n times and the n decoded layers are summed to form a layered image.

7 Claims, 1 Drawing Figure

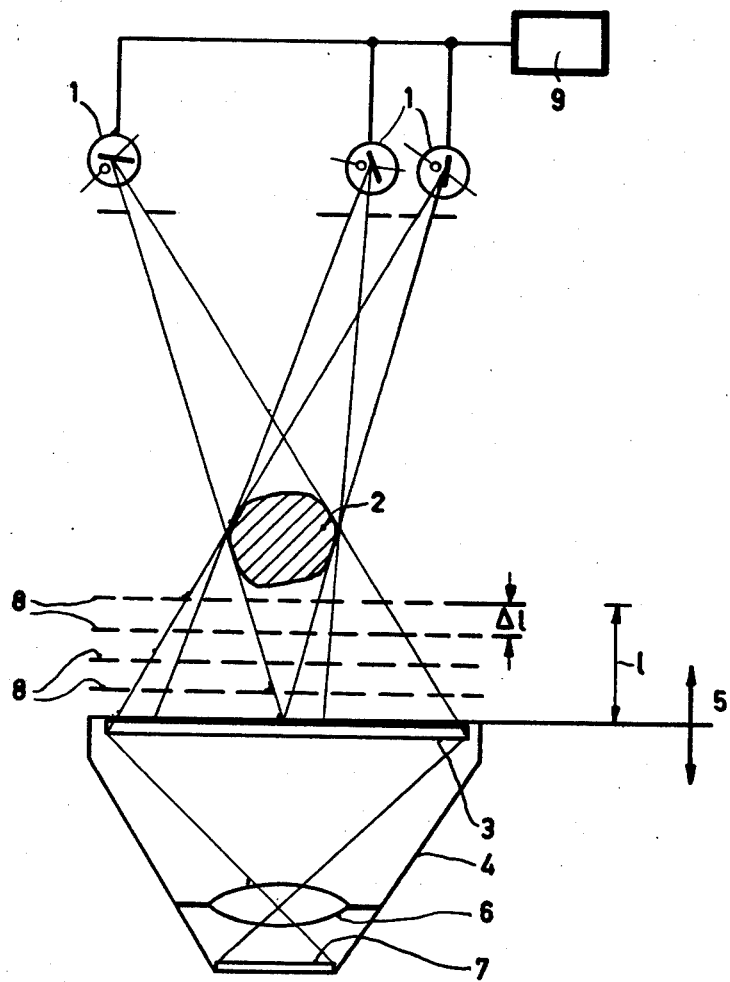

METHOD OF FORMING LAYERED IMAGES OF OBJECTS FROM SUPERPOSITION IMAGES OF DIFFERENT IMAGE PLANES

The invention relates to a method of forming a layered image of a three-dimensional object which is irradiated from different directions by a plurality of radiation sources.

U.S. Pat. No. 3,499,146 describes a method where object layers can be decoded from a number of simultaneously recorded simultaneous-superposition images of an irradiated three-dimensional object. This method enables three-dimensional reconstruction of an object by the formation of a layered image. The recording of the simultaneous-superposition images on X-ray films which are arranged one underneath the other, however, is not efficient.

The present invention has for its object to record a three-dimensional object, irradiated simultaneously from a number of directions, so that separate coded superposition images are formed in different image planes, and that given layers of the object are decodable.

This object is achieved in accordance with the invention in that on a mechanically moved detector face n coded superposition images of a single movement phase are sequentially recorded in different image planes. The decoding of the n superposition images so that these images are successively electronically superposed and summed, is realized by means of a coordinate matrix whose coordinates correspond to the geometry of the radiation source distribution, for a number of times which equals the number of radiation sources, with the result that each time the same layer of the object is decoded n times and the n decoded layers are summed to form a layered image.

The detector face is mechanically moved at a high speed, for example in milliseconds so that a number of coded superposition images of a single movement phase can be recorded in different image planes. The method can thus be used for the display of moving three-dimensional objects such as the beating heart. The all layers of moving object recorded during a movement phase can subsequently be decoded.

Because the formation of the layered image is realized so that the coded superposition images recorded in the various image planes are successively electronically superposed in a shifted manner and summed for a number of times which equals the number of radiation sources, a layer of the object is multiply decoded and the number of decoded layers is summed to form a layered image. The layered image formed from a plurality of coded superposition images in different image planes, has an advantage over the single decoded layer of a superposition image in that the signal-to-noise ratio is better; in comparison with the simultaneous method it has the advantage that the complex recording on X-ray films is eliminated.

The drawing diagrammatically shows an embodiment for sequential recording of coded superposition images. The object 2 in the FIGURE is simultaneously irradiated by a plurality of X-ray sources 1, a superposition image thus being formed on the flat entrance screen 3 of an electro-optical image converter 4. Continuous or intermittent movement of the image converter 4 in the direction 5 within the recording range $\iota$ produces a continuously or intermittently changing superposition image on the entrance screen 3. The coded superposition images are transferred from the entrance screen 3 to the output screen 7 via an optical or electronic lens 6, and are optically or electronically stored therefrom. The superposition images of the different image planes 8 with the distances $\Delta \iota$ can be recorded in different manners.

In the case of continuously switched on X-ray tubes 1, the coded superposition images are derived from the output screen 7 with the normal image frequencies of the optical or electronic recording devices.

Alternatively, it is possible to flash the X-ray tubes 1 by means of a control unit 9 during the movement of the image converter 4, the flashed superposition images being derived from the output screen 7 at the same time. By fast movement of the image converter in the direction 5 within the recording range $\iota$, a number of recordings of a movement phase can be made. Alternating movement of the image converter also enables cinematographic recording of coded superposition images of moving objects.

The superposition images which appear as shadow images on the detector face can also be recorded and stored with the aid of optical means.

What is claimed is:

1. A method of forming a layered image of a three-dimensional object which is irradiated from different directions by a plurality of radiation sources, comprising the steps of sequentially recording n coded superposition images of a single movement phase on a mechanically moved detector face in different image planes and decoding the n superposition images by successive electronic superposition and summation by means of a coordinate matrix whose coordinates correspond to the geometry of the radiation source distribution, for a number of times which equals the number of radiation sources, whereby the same layer of the object is decoded n times and the n decoded layers are summed to form a layered image.

2. A method as claimed in claim 1, wherein the radiation sources are X-ray tubes, operating in a pulsed mode, which produce superposition images in different image planes on a continuously moving detector face.

3. A method as claimed in claim 1, wherein the detector face is rapidly moved to and fro, and during each movement phase n coded superposition images are formed.

4. A method as claimed in claim 1 wherein the detector face comprises the entrance screen of an X-ray image intensifier tube.

5. A method as claimed in claim 1 wherein the detector face comprises a flat luminous screen.

6. A method as claimed in claim 1 wherein the superposition images appearing on the detector face are recorded and stored by electronic means.

7. An apparatus for carrying into effect the method of claim 1 comprising a detector having an image plane which is movable with respect to an object position and a plurality of X-ray sources disposed in a fixed geometry with respect to said object position.